(12) United States Patent
Battiston et al.

(10) Patent No.: US 7,389,679 B2
(45) Date of Patent: Jun. 24, 2008

(54) MEASUREMENT CELL AND METHOD FOR THE ANALYSIS OF LIQUIDS

(75) Inventors: Felice M. Battiston, Muttenz (CH); Peter Haier, Unterschleissheim (DE)

(73) Assignee: Concentris GmbH, Basel (CH)

( * ) Notice: Subject to any disclaimer, the term of this patent is extended or adjusted under 35 U.S.C. 154(b) by 318 days.

(21) Appl. No.: 11/230,852

(22) Filed: Sep. 20, 2005

(65) Prior Publication Data

US 2006/0065046 A1 Mar. 30, 2006

(30) Foreign Application Priority Data

Sep. 24, 2004 (DE) .................. 10 2004 046 685

(51) Int. Cl.
*G01N 29/00* (2006.01)
(52) U.S. Cl. .................... 73/61.79; 356/501
(58) Field of Classification Search ............... 73/64.56, 73/61.41, 61.79, 53.01; 137/144; 128/200.25; 356/501
See application file for complete search history.

(56) References Cited

U.S. PATENT DOCUMENTS

| | | | |
|---|---|---|---|
| 4,061,031 A | 12/1977 | Grimsrud | |
| 5,112,492 A * | 5/1992 | Ransohoff | .................. 210/656 |
| 6,176,903 B1 | 1/2001 | Wamsiedler | |
| 6,214,129 B1 * | 4/2001 | Nakaoka et al. | ................. 134/3 |
| 6,575,020 B1 * | 6/2003 | de Charmoy Grey et al. | ................................ 73/54.23 |
| 7,105,301 B2 * | 9/2006 | Su et al. | ......................... 435/6 |
| 7,260,980 B2 * | 8/2007 | Adams et al. | ............... 73/31.05 |

FOREIGN PATENT DOCUMENTS

DE 196 20 591 A1 11/1997
WO 01/22056 A1 3/2001

OTHER PUBLICATIONS

Godin, Michel. "Combined In Situ Micromechanical Cantilever-Based Sensing and Ellipsometry". Review of Scientific Instruments, vol. 74, No. 11 (Nov. 2003): 4902-4907.*

* cited by examiner

*Primary Examiner*—Hezron E. Williams
*Assistant Examiner*—Mark Shabman
(74) *Attorney, Agent, or Firm*—Renner, Otto, Boisselle & Sklar, LLP

(57) ABSTRACT

This invention relates to a liquid measurement cell for micromechanical sensors, so-called cantilever sensors. These sensors are e.g. used for the detection of biomolecules without the need for fluorescent or radioactive labelling. These measurements are usually carried out in liquids, where air or gas bubbles present in the analyte inside the measurement cell can significantly affect measurement results or even destroy the sensor. In a measurement cell according to this invention, a closed gas volume is present above the liquid level. Consequently, gas or air bubble can be constantly absorbed by the gas volume and do not come in contact with the cantilever sensors. The measurement cell is further characterised by a very low volume in the order of microliters and can be combined with various optical or piezoelectrical/piezoresistive read-out methods.

20 Claims, 3 Drawing Sheets

MEASUREMENT CELL AND METHOD FOR THE ANALYSIS OF LIQUIDS

FIELD OF THE INVENTION

The present invention relates to the design of a liquid measurement cell or measurement chamber for micromechanical cantilever sensors and to the method of operating such a cell. Cantilever sensors have a high sensitivity and do not need any fluorescent or radioactive labels to detect biological molecules. These are two of the reasons why cantilever sensors attract increasing interest for detecting biomolecules or studying molecular interactions. The measurement cell according to the present invention is characterized by an extremely small sample volume and eliminates the problem of air bubbles in the sample. Such air bubbles often occur inside a liquid handling system and negatively affect measurements with cantilever sensors. In addition, the cantilever sensors are mechanically decoupled from the measurement cell. This minimizes the effect of acoustic reflections inside the measurement cell, when the oscillation properties of the cantilevers are measured. The measurement cell according to the present invention is especially well suited for signal readout using optical beam deflection, but may be used equally well for other signal detection methods.

DESCRIPTION OF THE PRIOR ART

When using cantilevers as biosensors, the cantilever is typically manufactured using microfrabrication techniques and designed as a cantilevered spring fixed to a solid support at one end and able to move freely at the other end. This cantilever is usually coated—or functionalized—with a specific receptor molecule able to selectively bind a certain target substance. This sensor is then typically brought into contact with the analyte liquid. If molecules of the target substance are present in the sample, they chemically bind to the receptor molecule on the sensor. This leads to a change of the surface stress on the cantilever and at the same time increases the mass load of the cantilever. While surface stress causes a small mechanical bending (deflection) of the cantilever, an increase in mass load typically decreases the resonance frequency of the cantilever. Both effects—the minimal deflection as well as changes in the oscillation properties—can be measured with high accuracy and used as indicator for the quantity to be measured.

Generally speaking, a mechanical change in the properties or behavior of the cantilever serves as a means of indication or detection. The high sensitivity of cantilever sensors is one particular advantage, which in many cases is difficult or even impossible to achieve with other methods.

Applications in the field of biology usually require highly specific interactions, e.g. antigen-antibody interaction or hybridization of complementary DNA strands. These applications are well established in the literature, as is illustrated by the following examples:

D. Charych et al. describe in PCT patent application WO 98/50773 (1997) the detection of (bio-)molecules based on the "key-lock-principle", i.e. by immobilizing specific binding partners of the target substance to be detected with the cantilever.

Similarly, T. Thundat et al. describe the detection of molecules based on antigen-antibody interactions in PCT patent application WO 00/58729 (1999) "Micromechanical Antibody Sensors".

In addition, M. K. Bailer et al. desribe in PCT patent application WO 0133226 the use of similarly functionalized reference cantilevers within a cantilever array under the title "Cantilever and Transducers". This differential measurement method, where deflections of different cantilevers within an array are compared to each other, allows more reliable and stable measurement by compensating undesired effects, e.g. variations in sample temperature, by subtracting a reference signal.

With respect to biological measurements, the following two approaches are known in the field:

In one setup, the cantilever or cantilever arrays including the support structure are mounted as a whole inside a closed measurement cell. One possibility is to detect the signal optically by the deflection of a light beam, which passes through a transparent cover of the measurement cell, is then reflected by the cantilever and finally hits a position sensitive detector. C. Prater et al. describe such an arrangement in PCT patent application WO 03038409. This design, however, requires a relatively large volume of the measurement cell, typically a few milliliters. This implies that an equally large volume of the often expensive analyte is needed for one measurement. Turbulences, which occur when measuring in flow-through mode, long diffusion paths and times, increased challenges with respect to temperature stabilization as well as a complicated procedure to exchanging the sensors are further significant drawbacks of this approach. When measuring in the dynamic mode, where in addition to the deflection of the cantilever its oscillation behavior is determined, an oscillation actuator—typically a piezoelectric element, which is driven by alternating voltage—is needed. In this setup the actuator has to be placed inside the liquid, which turns out to be another disadvantage: besides the electrical insulation of the actuator, the strong, direct coupling of the oscillator to the liquid and thereby the whole system may cause reflections and undesired resonances. This may significantly affect measurements in a negative way.

The second arrangement known in the state of the art is described e.g. in Grey et al., PCT patent application WO 00/66266, where cantilever sensors are integrated into microfluidic channels. While the volume of the measurement chamber can be significantly reduced in this way, the production of these complex structures is more difficult and therefore more expensive than the production of simple cantilever arrays. In addition, not all cantilevers can be exposed to the same liquid in this setup, i.e. they are not inside the same liquid volume. Therefore, reference measurements in order to account for unwanted effects resulting e.g. from temperature variations or unspecific bindings are less reliable. Finally, when integrating a cantilever into a microchannel, the methods for coating its surface are limited: these cantilevers can not be immersed into a glass capillary for functionalisation and usually only one side of the cantilever is accessible for functionalisation and/or passivation.

Additionally, both methods described above require that the liquid, which flows across the cantilevers, is freed from any air or gas bubbles before coming into contact with the cantilever. This is mandatory, because cantilevers are mechanical transducers and gas bubbles inside the liquid will exert a considerable force on the cantilever. The resulting distortions will adversely affect or falsify measurement results. In certain cases, the sensor or its surface coating can even be mechanically destroyed. When using cantilever technology, the problem of bubble formation is increased insofar as air bubbles preferably form at edges. The geometry of a cantilever structure alone makes it inherently impossible to avoid such edges.

Precipitators for the absorption of gas bubbles are known in principle, e.g. from U.S. Pat. No. 4,061,031 by Grimsrud, wherein the combination of a gas precipitator with an apparatus for the measurement of flow rates is disclosed. In this case, the gas volume inside the precipitator is closed but divided into two chambers by a vertical separating plate. The measurement of the flow rate is achieved by comparing the liquid levels inside these two chambers. There is no mentioning of any other use of this arrangement, especially relating to the addition of a cantilever sensor or similar measurement setup. Furthermore, the inlet and outlet are vertical, which would be very inconvenient with respect to the purpose of the present invention. In addition the gas volume is smaller than the liquid volume, i.e. relatively large changes in pressure occur, when the gas volume is increased or decreased. In contrast, the present invention relies on a preferably constant gas pressure, which is achieved by using a comparably large gas volume.

SUMMARY OF THE INVENTION

The invention described below comprises a measurement chamber or measurement cell, which combines an extremely small chamber volume with a device or arrangement, which prevents the formation of air or gas bubbles. Other than in the prior art, the cantilevers are neither placed completely inside the measurement chamber and thereby within the analyte liquid, nor does the invention make use of complicated microfluidic channel structures. According to the invention however, the cantilever or cantilevers are mounted in a way that only the cantilever itself and not its support are in contact with the liquid. This allows to keep the volume of the measurement cell very small, typically a few microliters.

In order to eliminate unwanted air bubbles, a closed gas volume able to accommodate incoming air or gas bubbles is situated above the liquid. This principle makes use of the fact that gas bubbles inside a liquid move upwards due to gravity.

In a typical embodiment the cantilever is inserted into the measurement chamber from above until the cantilever itself is fully immersed into the liquid and the support touches the liquid surface or is partially immersed into the liquid. The cantilever or cantilevers can further be fixed to an additional holder which seals up the measurement cell thereby defining the gas volume above the liquid.

In a special embodiment an oscillator, preferably in the form of a piezo element, can be fixed to one part of the above-mentioned holder which is not in contact with the liquid. This oscillator can then be used to excite resonances of the cantilever in order to determine its fundamental frequency or higher harmonics.

In order to protect the piezo element against contact with the liquid, an additional seal, e.g. in the form of a membrane, can be attached between the piezo element and the cantilever array. This seal is preferably chosen not to or to only slightly affect the coupling of the piezo oscillation to the cantilever.

In an embodiment of the invention the gas volume of the measurement cell above the liquid is at least 10 to 20 times larger than the liquid volume. This ensures that enough gas can be accommodated without the pressure becoming too large.

In a typical embodiment the liquid volume amounts to only a few microliters and the inner diameter of the measurement chamber is of the order of one millimeter.

Another embodiment combines the measurement cell according to this invention with a system for the detection of the cantilever movement (deflection, resonance frequency). In a preferred embodiment the movement of the cantilever is detected optically by the deflection of a light beam, especially a laser beam (beam deflection method). Hereby the beam hits the free end of the cantilever and is reflected onto a detector which determines the position of the incident light beam with high precision. When using multiple cantilevers, e.g. inside a cantilever array, multiple light sources and/or multiple detectors can be used for parallel signal read-out. In another embodiment, multiple light sources can be combined with one detector, whereby the light sources are turned on and off sequentially measuring the cantilever signals sequentially (time-multiplexing). If desired, additional optical elements can be used e.g. for focussing the light beam. In a similar way, one detector can be combined with either a moveable light source and/or moveable optics which scan the cantilevers and sequentially determine the movement of each cantilever.

An arrangement of multiple cantilevers allows for instance the parallel detection of different substances or the use of reference sensors for control purposes and for increased reliability of the measurement.

A special extension of the embodiment described above is the use of an additional light source which is focussed either on a part of the cantilever support inside the liquid, or a—compared to the cantilever—inelastic structure, which e.g. may be designed in the form of a cantilever having the same thickness as the support. The signal reflected by this structure can be used as a reliable indicator of distortions such as a change in the refraction index of the liquid.

In other embodiments, the movement of the cantilever or cantilevers can be detected interferometrically or using an electrical signal generated by the cantilever itself, e.g. when using a piezo-resistive or piezo-electric cantilever.

In another embodiment the measurement cell according to this invention can be combined with a liquid handling system which moves the analyte liquid through the measurement cell in a controlled way. It is convenient to use tubes with a diameter similar to that of the measurement cell for the inlet and the outlet of the measurement cell. The liquid handling system may allow measurements in "flow-through" and/or "stop-and-go" mode.

The liquid handling system mentioned above can be combined with other, similar arrangements to eliminate gas bubbles, e.g. by placing one or more gas reservoirs along the inlet tube.

In a special embodiment of the liquid handling system, which ideally can be combined with the measurement cell according to this invention, the liquid is drawn by a pump from a reservoir through the measurement cell, i.e. the pump is located behind the measurement cell. This has the advantage that no over-pressure can form inside the system—even if a tube is clogged or another defect occurs, no liquid will leak from the system. In this embodiment, the gas volume of the measurement cell is hermetically sealed from the environment, i.e. the gas volume is closed.

Another special embodiment includes the combination of the measurement cell according to the invention and/or—if present—its inlet tube with an arrangement for temperature control. Controlling the temperature not only allows to precisely define the measurement parameters but also to influence the diffusion of air bubbles out of the liquid.

An arrangement according to this invention may be used to detect or quantify bio molecules, e.g. DNA, proteins, active ingredients etc. in liquids. Typically, the cantilever or cantilevers are coated with different receptor molecules, which are selected according to the target substance to be detected. The use of a cantilever or cantilevers for the detection of microorganisms, reactions in cells or chemical substances in liquids are further possibilities.

With time-resolved measurements, the time-dependent data can be used for the determination of binding constants, association or dissociation constants.

Typically the following measurement procedures are used:
(1) The analyte liquid is transported into the measurement cell. As soon as the liquid volume has been filled, the liquid flow is stopped and the measurement of the cantilever movement (deflection and/or oscillation properties) is started. After the measurement, the liquid is removed from the measurement cell. One or more cleaning steps before and/or after the measurement can be included in the procedure.
(2) The measurement is performed, while the liquid flows through the measurement cell, preferably at a constant flow rate. The cantilever movement is recorded at the same time. One or more cleaning steps before and/or after the measurement can be included in this procedure as well.

Further embodiments of the apparatus and method according to this invention can be drawn from the following descriptions and the appended claims.

DESCRIPTION OF THE DRAWINGS AND OF EMBODIMENTS

One example of a particular embodiment of the invention will be more closely described on the basis of the following figures.

Figure 1:
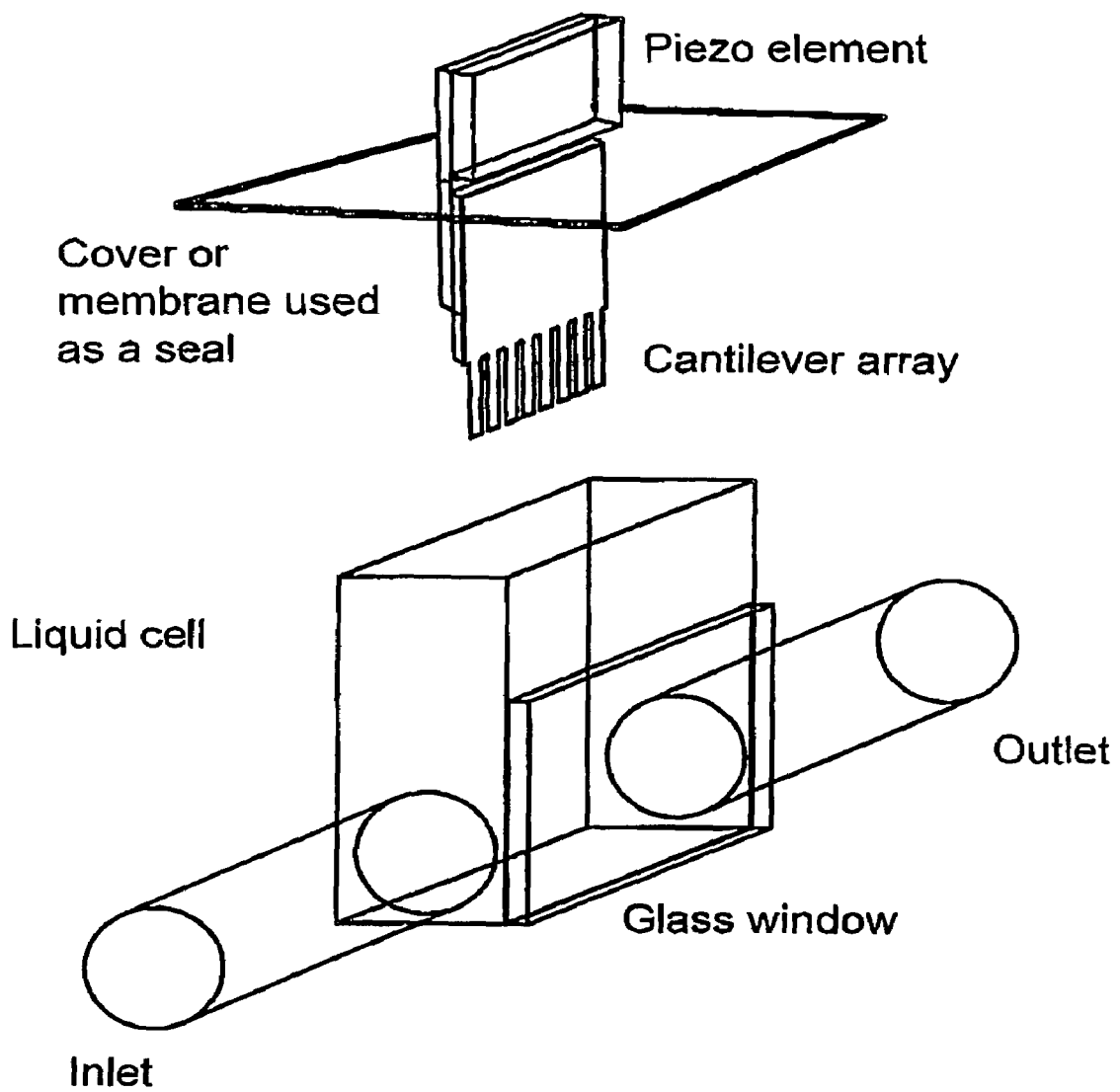
FIG. 1 depicts a schematic arrangement of a measurement cell according to the invention.

FIG. 1 schematically shows an arrangement according to the invention. The arrangement comprises a liquid cell with an inlet and an outlet for the analyte liquid. If the movement of the cantilever or cantilevers is detected optically, one side of the measurement cell contains a transparent cover, in this case a glass window. This window can either be flat, as shown in FIG. 1, or curved in a way that the incoming as well as the outgoing light beam hit the surface at a 90 degree angle in order to minimize effects resulting from refraction at the interface. The cantilever array is mounted on a holder which contains a cover that acts as an air-tight seal of the measurement cell when the holder is inserted into the cell. If, as shown in the figure, a piezo element is attached to the holder, the cover can be in the form of a membrane, which on one hand protects the piezo element from coming into contact with the liquid and on the other hand only minimally damps the excitation of the cantilever oscillation.

Figure 2:
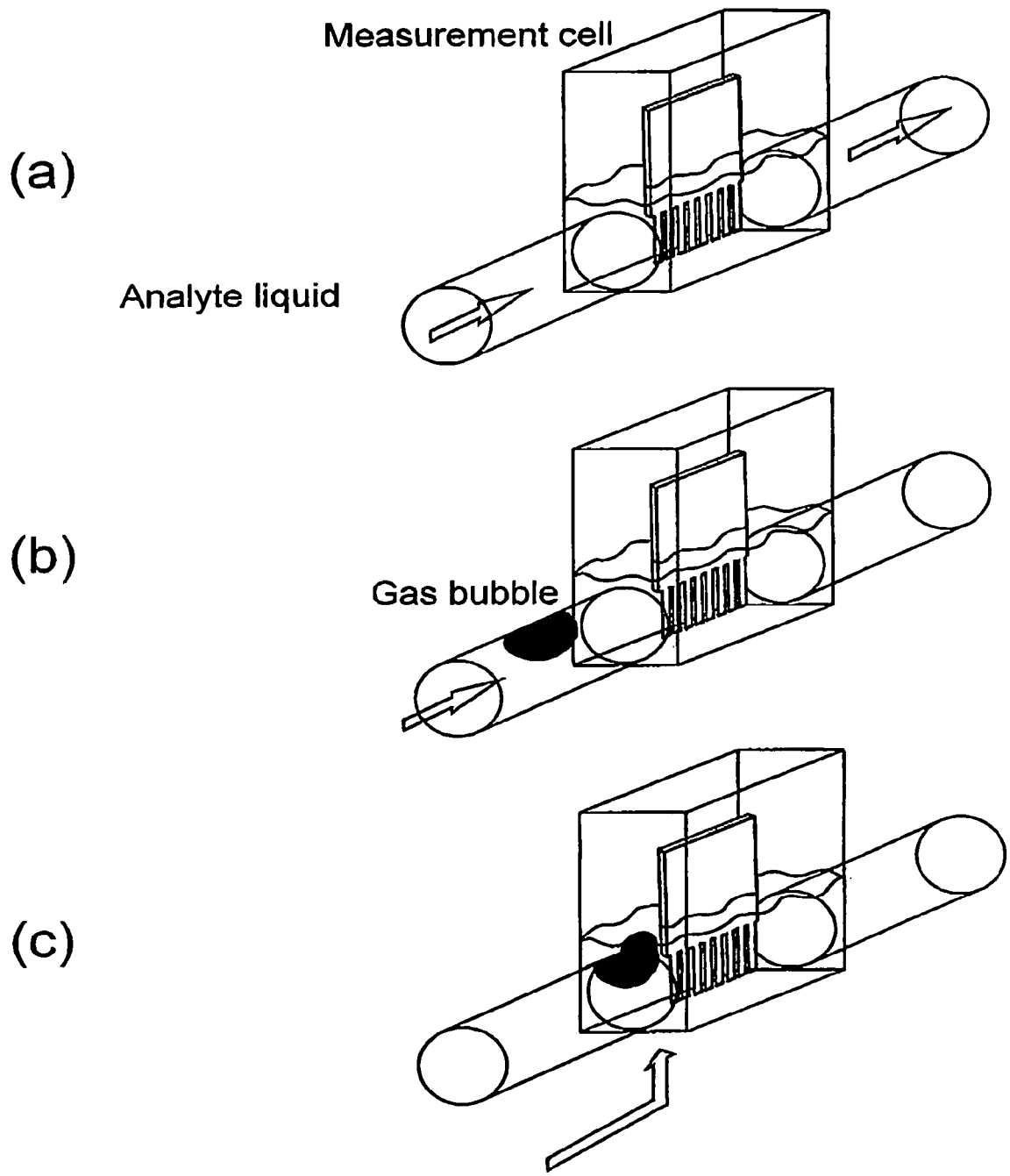
FIG. 2 illustrates the working principle of the measurement cell.

FIGS. 2(a) to 2(c) illustrate the working principle of the measurement cell according to the invention.

FIG. 2(a) depicts the setup of the measurement cell with inlet and outlet as well as a cantilever array partially immersed into the analyte liquid. A closed gas volume is present above the liquid level. A gas bubble (dark), which is inside the liquid handling system and transported towards the measurement cell is shown in FIG. 2(b). FIG. 2(c) illustrates how the air bubble moves upwards when entering the measurement cell through its inlet port and is finally absorbed by the gas volume above the liquid level. Therefore, the air bubble does not influence or compromise the measurement in any way.

Figure 3:
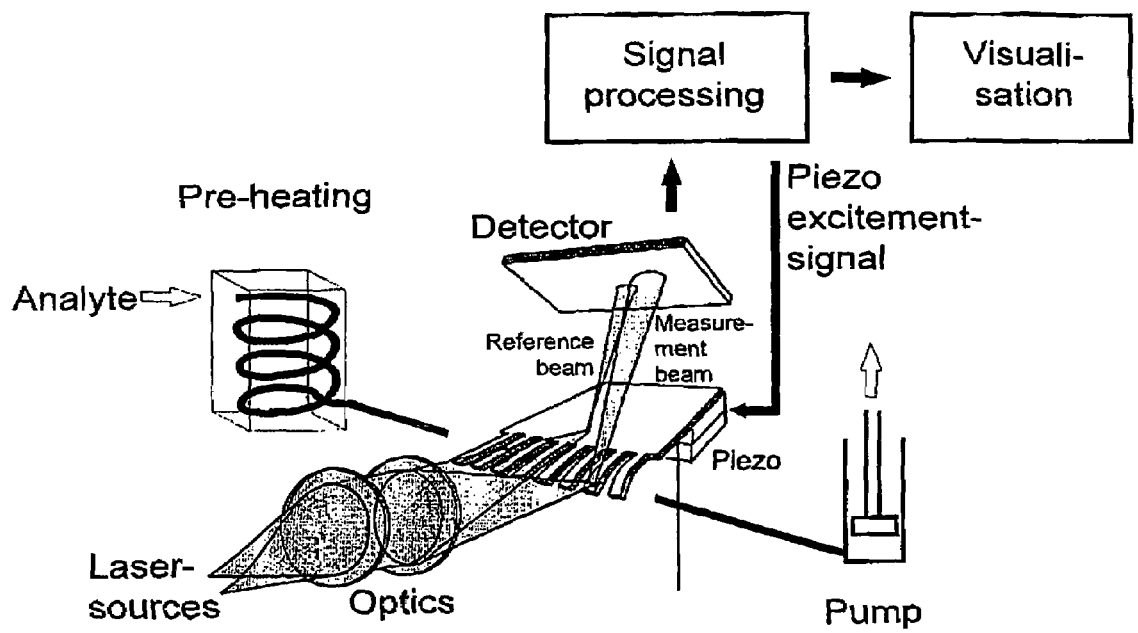
FIG. 3 shows a block diagram of different components of an arrangement according to the invention.

FIG. 3 shows a block diagram with different parts of an arrangement according to the invention. The cantilever—or the array of cantilevers, respectively—generates electrical signals resulting as a consequence of the deflection of one or more laser beams on a detector, which electrical signals indicate the current deflection of each cantilever. Additional use can be made of a reference laser beam which is focussed on the cantilever support and allows e.g. to detect and account for effects caused by a change in the refractive index of the analyte liquid. The electrical signal from the detector is processed and visualised using well-known techniques. In the case of dynamic mode measurements (i.e. determination of the oscillation properties of the cantilevers) the signal is conveniently also used to excite the oscillation of the cantilever (s). In addition, the figure schematically shows the sample inlet equipped with a temperature stabilisation as well as a pump, which transports the analyte liquid through the measurement cell.

The measurement functions described above can easily be implemented by a person skilled in the art. Commercial software is available for many partial functions; where such software is not commercially available, it can easily be implemented by someone skilled in the art.

The invention claimed is:

1. A measurement cell for an arrangement for the analysis of liquids, comprising, integrated into a single cell:
at least one inlet and at least one outlet for the analyte liquid,
a gas volume for the absorption of gas bubbles present inside the analyte liquid, said gas volume being located within said single cell and sealed from the environment,
at least one micromechanical cantilever, which is at least partially located inside the measurement cell and is at least partially in contact with the analyte liquid.

2. The measurement cell according to claim 1, wherein the sealed gas volume is a multiple of the liquid volume inside the measurement cell, particularly at least a 10 times multiple.

3. The measurement cell according to claim 1, wherein the inlet and the outlet are located below the liquid level, and the gas volume is located above the liquid level.

4. The measurement cell according to claim 1, wherein the at least one micromechanical cantilever is inserted into the measurement cell from the top of the measurement cell so that at least a part of said cantilever is in direct contact with the analyte liquid.

5. The measurement cell according to claim 1, further comprising a holder to which the at least one micromechanical cantilever is fixed, said cantilever and its holder being removable from said measurement cell and/or exchangable.

6. The measurement cell according to claim 4, wherein the at least one micromechanical cantilever and/or a holder of said micromechanical cantilever seal the measurement chamber from the environment.

7. The measurement cell according to claim 1, further comprising means for detecting the movement of the at least one micromechanical cantilever, this detection being at least one of optical, interferometric, piezo-resistive or piezo-electrical.

8. The measurement cell according to claim 7, further comprising
a first light or laser beam for detecting a deflection or a movement of the at least one micromechanical cantilever, and
a second light or laser beam for determining a refractive index of the analyte liquid, said second light or laser beam being equal or similar to said first light or laser beam.

9. The measurement cell according to claim 8, wherein the second light or laser beam is deflected by the cantilever support or by an additional, rigid cantilever.

10. The measurement cell according to claim 1, further comprising means for temperature-controlling said measurement cell and/or the inlet tube.

11. The measurement cell according to claim 1, further comprising means for transporting the liquid through the measurement cell connected to said measurement cell.

12. The measurement cell according to claim 5, further comprising means for exciting oscillations of the cantilever, particularly a piezo element, said exciting means being fixed to the holder.

13. The measurement cell according to claim 12, wherein a first volume within said measurement cell, said first volume containing the at least one cantilever is sealed, preferably air-tight sealed, by a flexible membrane from a second volume containing the means for exciting oscillations.

14. The measurement cell according to claim 1, wherein the at least one cantilever is adjustable individually, in groups or together inside the measurement cell.

15. A method for analysing liquids inside a measurement cell containing at least one micromechanical cantilever, comprising the following steps:
   an analyte liquid being transported into said measurement cell through at least one inlet located below a liquid level inside the measurement cell,
   air bubbles within said liquid being adsorbed by a closed gas volume inside said measurement cell, said closed gas volume being situated above said liquid level and being sealed from an environment, and
   said liquid being transported out of said measurement cell through at least one outlet, said outlet being located below the liquid level.

16. The analysing method according to claim 15, whereby the at least one cantilever is at least partly immersed into the liquid from above.

17. The analysing method according to claim 15, wherein the analyte liquid is transported into the measurement cell and the transport stopped for a measurement.

18. The analysing method according to claim 15, wherein the analyte liquid is transported through the measurement cell at an approximately constant flow rate or constant speed during the measurement.

19. The analysing method according to claim 15, wherein the analyte liquid is sucked through the measurement cell, preferably by a pump situated at the outlet of said measurement cell.

20. The analysing method according to claims 15, wherein the analyte liquid is heated before and/or inside the measurement cell in order to raise the diffusion speed of the gas bubbles.

* * * * *